(12) United States Patent
Sharp et al.

(10) Patent No.: US 6,616,632 B2
(45) Date of Patent: Sep. 9, 2003

(54) CANNULA FOR USE WITH A MEDICAL SYRINGE

(75) Inventors: Fraser R. Sharp, Vancouver (CA); Neil Sheehan, Palo Alto, CA (US)

(73) Assignee: Inviro Medical Device Ltd., Bridgetown (BB)

( * ) Notice: Subject to any disclaimer, the term of this patent is extended or adjusted under 35 U.S.C. 154(b) by 0 days.

(21) Appl. No.: 10/152,981

(22) Filed: May 23, 2002

(65) Prior Publication Data

US 2002/0165504 A1 Nov. 7, 2002

Related U.S. Application Data

(63) Continuation-in-part of application No. 09/590,681, filed on Jun. 9, 2000, now Pat. No. 6,394,979.

(51) Int. Cl.⁷ .......................... A61M 5/00; A61B 19/00
(52) U.S. Cl. ........................ 604/117; 604/264; 604/411
(58) Field of Search .................... 604/117, 164, 604/272, 239, 523, 274, 39, 411–414

(56) References Cited

U.S. PATENT DOCUMENTS

| | | |
|---|---|---|
| 2,187,259 A | 1/1940 | Barnhart |
| 4,735,612 A | 4/1988 | Chevalier |
| 4,861,341 A | 8/1989 | Woodburn |
| 4,869,259 A | 9/1989 | Elkins |
| 5,071,413 A | 12/1991 | Utterberg |
| 5,100,394 A | 3/1992 | Dudar et al. |
| 5,158,084 A | 10/1992 | Ghiatas |
| 5,199,441 A | 4/1993 | Hogle |
| 5,364,373 A | 11/1994 | Waskonig et al. |
| 5,409,004 A | 4/1995 | Sloan |
| 5,484,423 A | 1/1996 | Waskonig et al. |
| 5,752,969 A | 5/1998 | Cunci et al. |
| 5,797,897 A | 8/1998 | Jepson et al. |
| 5,993,411 A | 11/1999 | Choi |
| 6,010,486 A | 1/2000 | Carter et al. |
| 6,033,386 A | 3/2000 | Novacek et al. |
| 6,224,608 B1 | 5/2001 | Ciccolella et al. |

FOREIGN PATENT DOCUMENTS

| | | |
|---|---|---|
| DE | 1491866 | 10/1969 |
| DE | 2544109 | 4/1977 |
| EP | 0819443 | 1/1998 |
| FR | 2758462 | 7/1998 |
| WO | PCT/US90/01350 | 10/1990 |

Primary Examiner—Sharon Kennedy
(74) Attorney, Agent, or Firm—Nixon & Vanderhye

(57) ABSTRACT

A blunt needle plastic cannula for a syringe has a central axial passage terminating in a tip opening axially through one end thereof. Different axial sections along the cannula have respective differential resistances to movement relative to a membrane upon insertion of the cannula into the membrane. The opposite end of the cannula may have a Luer fit or Luer lock or may have integrally formed therewith an adapter for releasably connecting the adapter and cannula to the distal end of the barrel of the syringe. A syringe plunger and the adapter have connective structure whereby the adapter and cannula can be withdrawn into the interior of the barrel. The opposite ends of the barrel are sealed by portions of the plunger.

21 Claims, 11 Drawing Sheets

FIG. 1
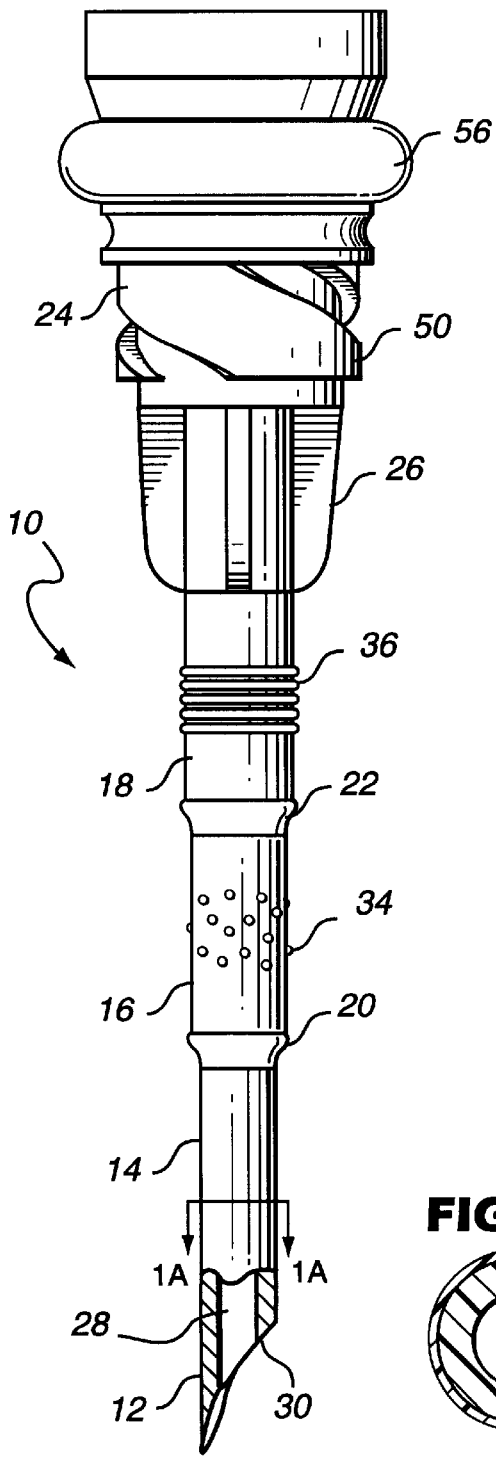
FIG. 2
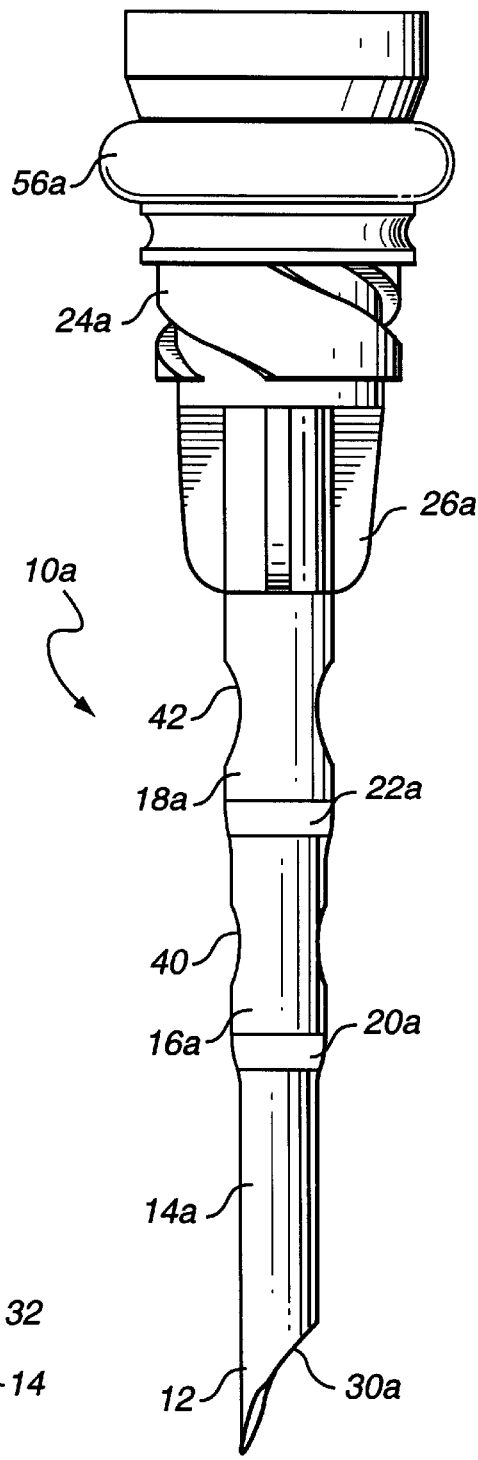
FIG. 1A

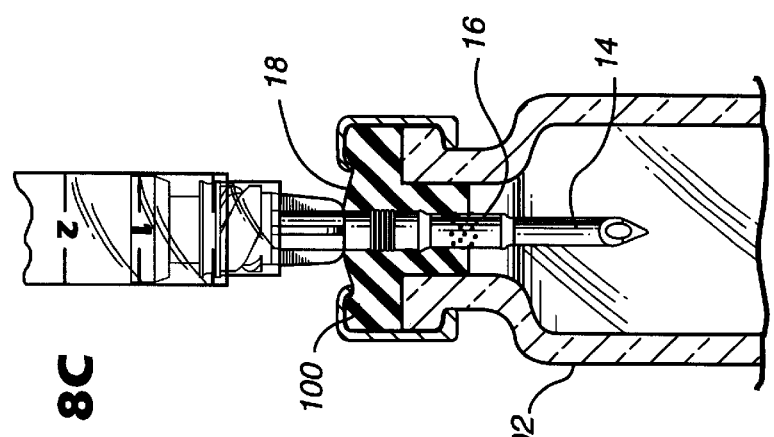
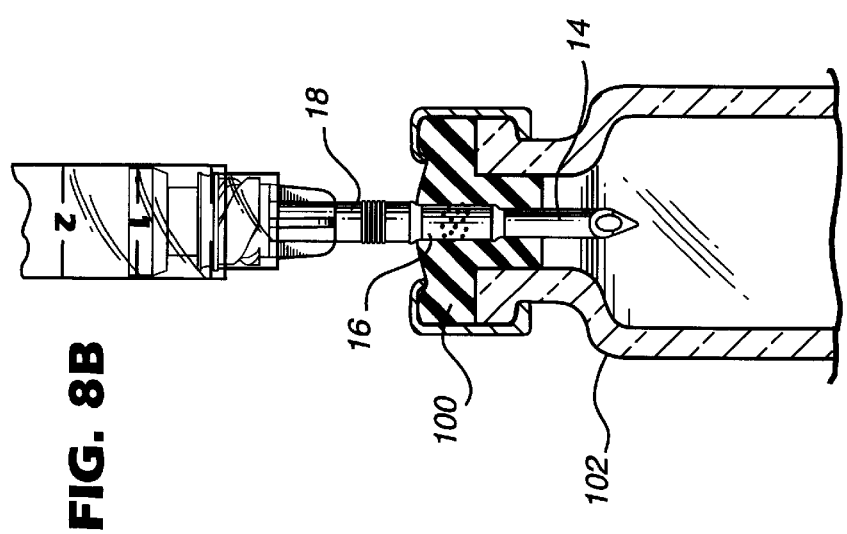
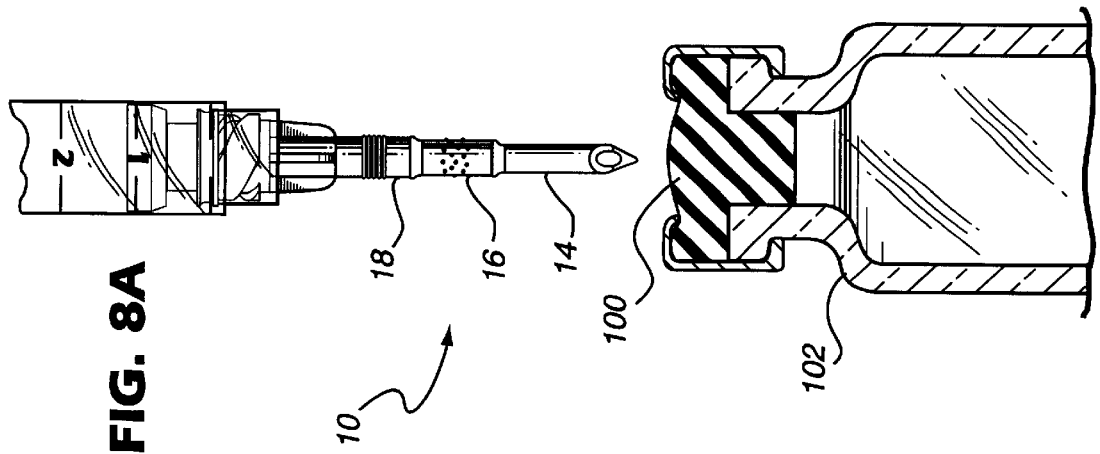

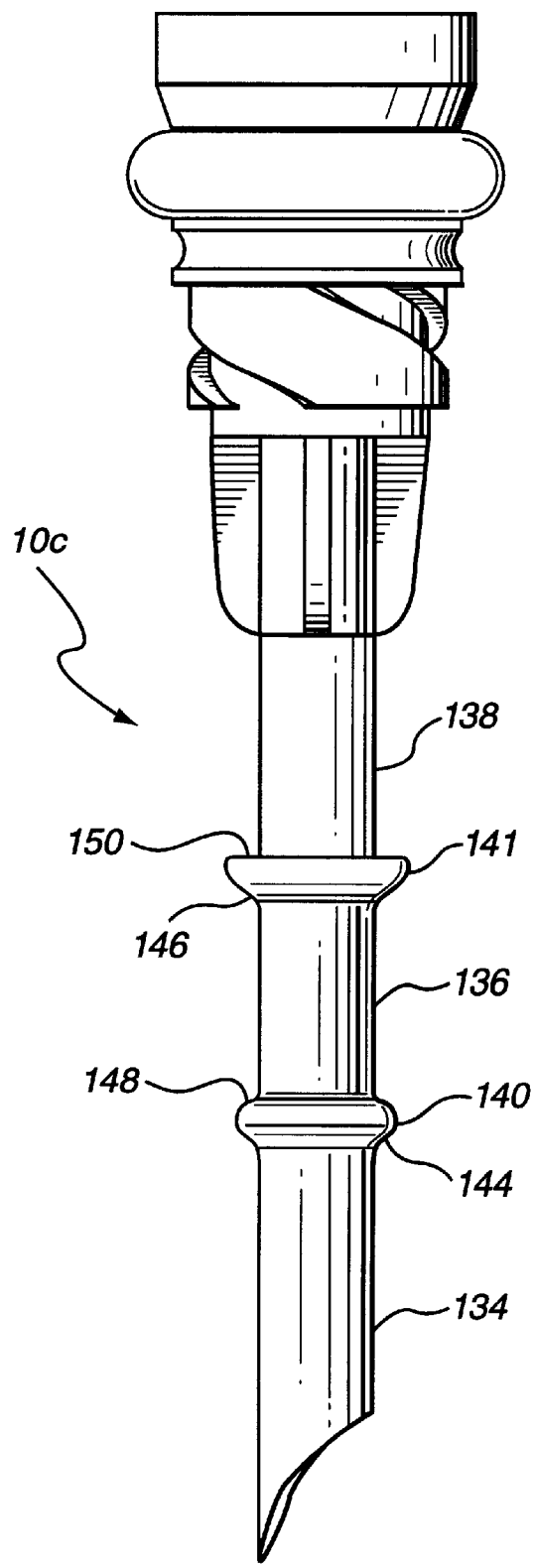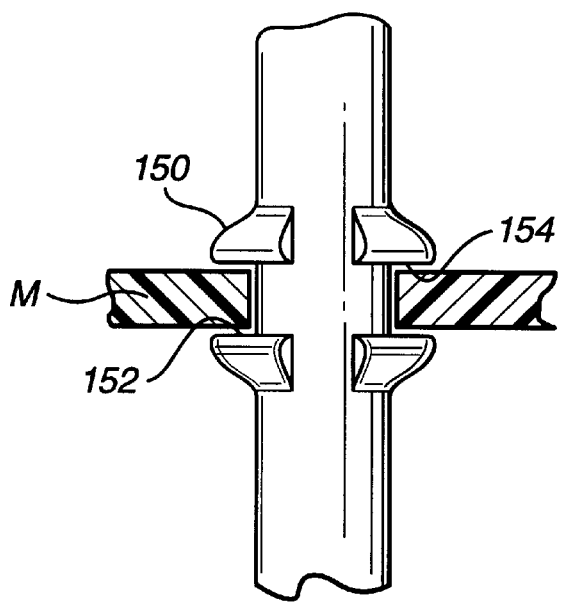

CANNULA FOR USE WITH A MEDICAL SYRINGE

RELATED APPLICATIONS

This application is a continuation-in-part of application Ser. No. 09/590,681, filed Jun. 9, 2000, now U.S. Pat. No. 6,394,979, issued May 28, 2002.

BACKGROUND OF THE INVENTION

The present invention relates to a cannula for use in the medical field and particularly relates to a cannula useful with a syringe for penetrating membranes or septums, pre-slit or non-pre-slit, as commonly used in medications vials, intravenous bags, access ports and the like. Such penetration allows for aspiration or injection from or into a wide variety of containers.

Syringes used in the medical field usually have a metal needle mounted at the front of the barrel allowing for aspiration of fluid into the syringe and subsequent injection into the patient through the skin, or indirectly through a previously placed intravenous infusion line. Access to those lines is provided by a variety of devices called access ports. These access ports are primarily of two types, one with an intact septum or membrane and another which has been pre-slit to allow access by a completely blunt, usually plastic, cannula. Medication vials which do not have a pre-slit septum can be accessed by a blunt cannula using a separate valve or port which contains a pre-slit septum. This valve is inserted into and traverses the vial stopper allowing aspiration of the medication vial contents using a blunt cannula through the valve's pre-slit septum. Therefore, health care workers must use either a sharp metal needle for aspirating medication vials or alternatively use an access port, to allow aspiration and injection using a blunt plastic cannula. The use of this blunt cannula for non-pre-slit septums requires an additional device, extra time, effort and cost. There is therefore a need for a cannula which has sufficient sharpness and/or other features, to allow penetration of a pre-slit septum or puncturing a non-pre-slit septum but which is not sharp or strong enough to accidentally or easily puncture the health care worker's skin or a rubber glove protecting the hand. Such a cannula could be used for aspiration and injection through a variety of septums, membranes and other elastomeric stoppers without the need of additional access ports, spikes or other devices.

Additionally, after puncturing an access port in an IV line, the cannulas will be contaminated with fluid which may contain disease-causing viruses. Contact of this contaminated cannula with skin, damaged skin or mucous membrane can result in disease transmission. Also, during use of the cannula, the cannula, which has pierced a membrane, may be forced out of the membrane, e.g., if increased pressure is generated within a system, for example, by rapid injection of fluid. Alternatively, a full or partially filled syringe is sometimes left attached to the IV line by the needle inserted through a membrane, e.g., to allow titrating of additional aliquots of medication from the same syringe. The mechanical connection between a needle or plain cannula and an access port in an IV line is inevitably somewhat insecure.

BRIEF DESCRIPTION OF THE INVENTION

In accordance with a preferred embodiment of the present invention, there is provided a cannula for a syringe which has (1) a piercing component or section for piercing non-pre-slit septums, such as vial stoppers, or entering pre-slit membranes, but which is sufficiently blunt to avoid penetration of a health care worker's skin or surgical gloves; (2) a passage through the cannula with an axial opening to prevent lateral emission of fluids, when expressing fluid from a syringe as the accurate dose of medication is prepared as is common practice with needles; and (3) discrete sections or components along the length of the cannula having different resistances, frictional or otherwise relative to a septum enabling a single cannula to be retained within a septum of different characteristics, e.g., thickness or hardness as a function of the extent of penetration of the cannula through the septum. To accomplish the first objective, the piercing section of the cannula, which is formed of a plastic material, is preferably smooth-sided, of relatively narrow diameter and has an inclined pointed surface or surfaces sufficient to penetrate both non-pre-slit and pre-slit septums. The cannula, however, has insufficient sharpness to easily or accidentally penetrate skin or surgical gloves (i.e., a supported flexible membrane. The tip of the piercing section preferably has a surface inclined approximately 20–45° with the central passage opening axially through the surface. To facilitate penetration, a coating may be applied along the length of the piercing section, e.g., which may be approximately one-half in length. The coating may comprise a lubricious material, e.g., silicone, or a surface coating such as Parylene.

To provide a cannula having a variable resistance to movement relative to a septum, second and possibly third sections are spaced axially from the piercing section and away from the tip of the cannula. The second section is preferably of a larger diameter than the piercing section and the third section is preferably, although not necessarily, of a larger diameter than the second. Thus, multiple sections of increased diameter in a direction axially away from the cannula tip are provided. The second section has mechanical formations, e.g., roughened or textured surfaces or barbs, ribs or indentations, or merely increased diameter to increase the frictional resistance to removal of the cannula from a septum. For example, for use with relatively thinner pre-slit septums, discrete projections may be formed on the second section to increase frictional resistance to withdrawing movement of the cannula from the thinner septum. The third and preferably larger diameter section is spaced axially further from the tip of the cannula from the septum. The latter may be used with thicker pre-slit septums or septums with a larger slit, i.e., the cannula would be inserted into the septum to a greater extent to locate this portion of the cannula with the higher coefficient of friction into engagement with the walls of the septum.

In another form hereof, portions of one or both of the second and third sections of the cannula, which preferably increase in diameter in a direction away from the tip of the cannula, have reduced diameter indentations or "waists." The change in diameter of the waists relative to remaining portions of the sections affords increased resistance to movement of the cannula relative to the septum. From the foregoing, it will be appreciated that the cannula may be inserted into various thicknesses or sizes of septums or septal slits and, depending upon the depth of insertion of the cannula, the resistance to removal of the cannula can be regulated. Thus, the present cannula mounted on a syringe can be positioned to resist pulling out of the septum to varying degrees. In addition to this feature, the cannula is also sufficiently sharp to pierce non-pre-slit septums, such as present on medication vials or evacuated containers for blood or other fluid collection. The cannula is, however, sufficiently blunt to substantially preclude accidental penetration through an individual's skin or medical gloves.

Additionally, while the cannula has insufficient sharpness to easily penetrate an individual's skin or surgical gloves, cannulas are contaminated after use with fluids and could, upon contact with mucous membranes, skin or damaged skin, facilitate the transmission of certain diseases. Consequently, the cannula is also configured for use with a retractable needle-type syringe in which the cannula can be retracted into the syringe barrel subsequent to use. Accordingly, the end of the cannula opposite the cannula tip may be formed in a number of different configurations such that the cannula can be coupled, e.g., by Luer-type connections with retractable needle-type syringes or be integral with syringe adapters used with other forms of retractable needle-type syringes to enable the cannula to be withdrawn into the syringe barrel. Thus, the opposite end of the cannula may have a Luer fit or Luer lock mechanism or be configured to mate with an adapter of a syringe for withdrawal into the syringe.

In a preferred embodiment according to the present invention, there is provided a cannula for use with a syringe and for insertion through a membrane, comprising a cannula body including an elongated sleeve and having a central axial passage therethrough for transmitting a fluid between opposite ends thereof, the sleeve terminating in a tip at one end with the passage opening axially through the tip, an opposite end of the sleeve adapted for connection with the syringe, mechanical formations formed on an outer surface of the cannula body along one of first and second axially spaced sections along the sleeve affording respective differential resistances to movement relative to the membrane as a function of the depth of penetration of the cannula body relative to the membrane, the first section being located axially intermediate the tip and the second section and a transition section between the first and second sections having a diameter larger than the diameters of the first and second section.

In a further preferred embodiment according to the present invention, there is provided a cannula for use with a syringe and for displacement through a membrane, comprising a cannula body including an elongated sleeve formed of a plastic material and having a central axial passage therethrough for transmitting a fluid between opposite ends thereof, the sleeve terminating in a tip at one end with the passage opening axially through the tip, an opposite end of the sleeve adapted for connection with the syringe, first and second axially spaced sections along the sleeve, the first section being located axially intermediate the tip and the second section, a transition section between the first and second sections having a diameter larger than the diameters of the first and second sections, the transition section having a first surface facing the tip and a second surface on a side thereof opposite the first surface, the first and second surfaces affording respective differential resistance to movement in opposite directions relative to the membrane.

In a further preferred embodiment according to the present invention, there is provided a cannula for use with a syringe and for displacement through a membrane, comprising a cannula body including an elongated sleeve and having a central axial passage therethrough for transmitting a fluid between opposite ends thereof, the sleeve terminating in a tip at one end with the passage opening axially through the tip, an opposite end of the sleeve adapted for connection with the syringe, first and second axially spaced ribs along the sleeve axially intermediate the tip and the opposite end of the sleeve, the ribs having diameters larger than the diameter of the sleeve, the ribs having first surfaces axially facing one another and second surfaces on sides thereof opposite the first surfaces, respectively, the first and second surfaces affording respective differential resistances to movement in opposite directions relative to the membrane, the first surfaces being shaped to releasably capture an opening through the membrane therebetween and affording greater resistance to movement of the cannula.

BRIEF DESCRIPTION OF THE DRAWINGS

FIG. 1 is a side elevational view of a cannula constructed in accordance with a preferred embodiment of the present invention;

FIG. 1A is a cross-sectional view thereof taken generally about on line 1A—1A in FIG. 1;

FIG. 2 is a view similar to FIG. 1 illustrating a further form of the present innovation;

FIGS. 8A, 8B and 8C are sequential views illustrating the cannula of FIG. 1 penetrating a non-pre-slit septum;

FIG. 12 is a view similar to FIG. 1 illustrating a further embodiment of a cannula; and FIG. 13 is a fragmentary elevational view of a cannula body with transition sections capturing a membrane.

DETAILED DESCRIPTION OF THE INVENTION

Figure 3:
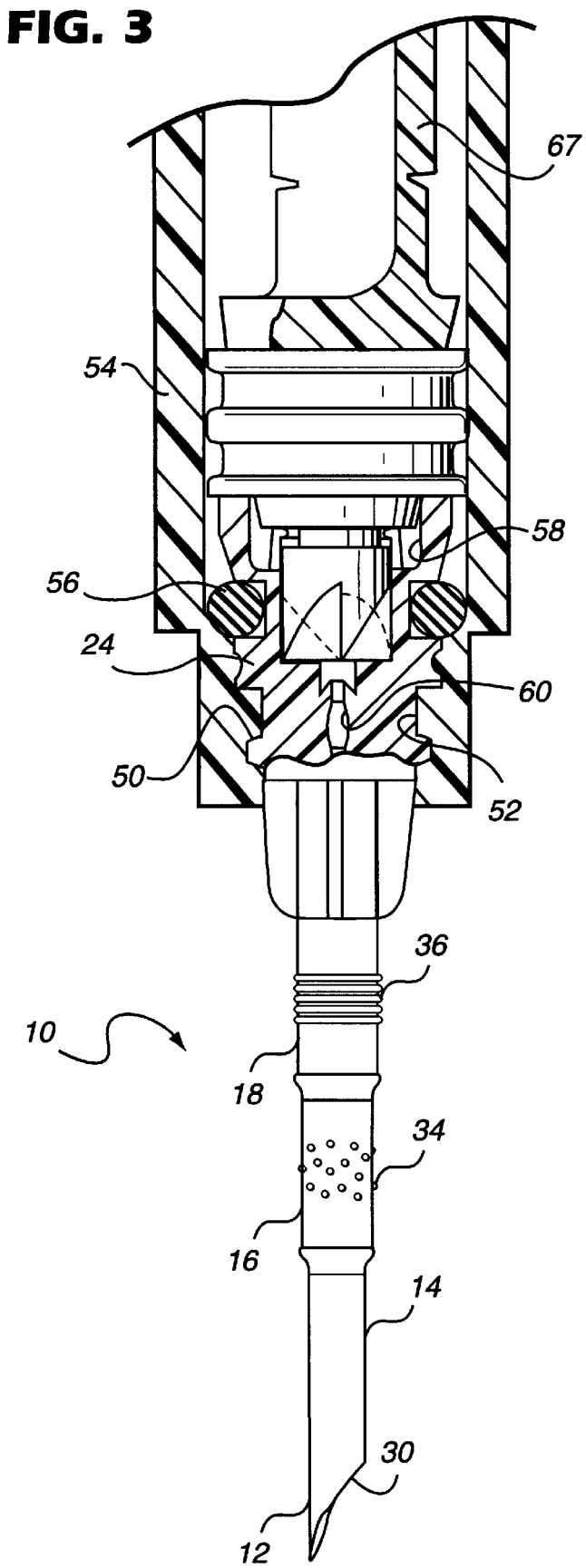
FIG. 3 is a fragmentary cross-sectional view of the cannula of FIG. 2 secured for use in the end of a syringe.

Referring now to the drawings, particularly to FIG. 1, there is illustrated a cannula, generally designated 10, preferably formed of a plastic material such as ABS or polycarbonate. The cannula 10 may also be formed of carbon fiber or metal. Cannula 10 includes a sleeve having a tip 12 at one end forming part of a piercing section 14 of the cannula. Piercing section 14 has the smallest diameter of cannula 10. A second section 16 is axially spaced from section 14 and has an increased diameter. Section 18 is axially spaced from both sections 14 and 16 and has a further increased diameter relative thereto. The sections 14, 16 and 18 are separated one from the other by transition sections 20 and 22, respectively, which are tapered inwardly in the direction of penetration of the cannula 10 through a membrane or septum. In the illustrated form, the transition sections 20 and 22 have slightly larger diameters than the diameters of the larger of the sections joined by the transition portions to provide a tactile feel when the cannula penetrates a septum and passes through the septum from one section to the next. The transition sections X also provide increased retention therein, i.e., increased resistance to withdrawal. In the form of cannula illustrated in FIG. 1, cannula 10 has its opposite end integrally formed as an adapter 24 for releasable securement to the distal end of a barrel as described hereinafter. Reinforcing struts 26 are provided about the circumference of the cannula 10, reinforcing the connection between the smaller diameter cannula sections and the integral adapter 24.

It will be appreciated that the illustrated and described cannula 10 comprises an elongated sleeve having a central axial passage 28 extending from the tip 12 throughout the length of the cannula 10 and through the adapter 24 for communication with the interior of a syringe barrel. The tip 12 of the cannula 10 has at least one angled surface 30, preferably about 20–45° relative to the cannula axis, through which the passage 28 opens. The piercing section 14 is preferably smooth-sided, of narrow diameter, for example, on the order of 0.070 inches, and is preferably coated with a material to reduce the friction between the cannula and a membrane, e.g., a septum, as the cannula penetrates the membrane, whether the membrane is a non-pre-slit or pre-slit septum. The coating 32 (FIG. 1A) may be any surface coating with a reduced coefficient of friction, as compared with the coefficient of friction of the base material, i.e., plastic. For example, the coating may be silicone or Parylene. This coating facilitates penetration of the piercing section through a membrane. The coating which may, for example, be Dow Corning MDX4-4159, may be applied throughout the length of the cannula or can be applied only to the piercing section 14.

The increased diameter second section 16 axially spaced from section 14 and tip 12 preferably has a surface which affords increased frictional resistance to movement of the cannula relative to a membrane, e.g., a septum, beyond that which is afforded by its increase in diameter relative to the piercing section 14. A coating or surface treatment, for example, an EDM (Electrical Discharge Machining) finish, can be applied to section 16 to afford such increased friction. Preferably, however, a plurality of discrete laterally extending, integrally formed projections 34 are disposed on the section 16. Projections 34 are spaced circumferentially and axially or randomly at different angles relative to one another along the length of and about section 16. It will be appreciated that upon insertion of cannula 10 into the membrane sufficiently to locate section 16 in contact with the membrane, the projections 34 engage the registering walls of the membrane and increase the resistance to withdrawal of the cannula from the membrane.

Referring to the third section 18, larger in diameter than both sections 14 and 16, further increased resistance to withdrawal of the cannula from a membrane is provided. Particularly, one or more outwardly projecting ribs 36 are provided on section 18. The ribs are preferably axially spaced one from the other along the cannula and may have arcuate or barbed surfaces in cross-section. For example, in axial cross-section along the length of the cannula, the ribs 36 may have arcuate semi-cylindrical surfaces. Alternatively, barbs may be provided having tapered surfaces facing in either or both axial directions or tapered surfaces facing one axial direction with an opposite surface normal to the axis of the cannula. Upon insertion of the cannula into a membrane locating the third section and particularly ribs 36 in frictional contact with the registering walls of the membrane, it will be appreciated that the ribs afford increased resistance to removal of the cannula from the membrane and permit the syringe mounting the cannula to be wholly supported by the frictional contact between ribs 36 and the penetrated walls of the membrane.

It will be appreciated that the various other types of mechanical formations or surface treatments, or both, may be provided on the various sections 14, 16 and 18 to afford increased resistance to movement and that one or more additional sections may be added or removed as necessary or desirable. Also, ribs similar to ribs 36 may be disposed on the second section 16 and the projections 34 may be disposed on the third section 18, with variations in their number and spacing depending on the level of increased frictional resistance desired. Alternatively, both sections 16 and 18 may have ribs, projections, EDM (Electrical Discharge Machining) or variable high grit surfaces or combinations of those surfaces. As indicated previously, the transition portions 20 and 22 provide tactile indication to the user of the extent of penetration of the cannula through the membrane and thus the user not only can visualize the depth of penetration of the cannula into the septum but can, by feel, recognize the depth of penetration. Thus, the transition portions 20 and 22, as well as the projections 16 and ribs 36, constitute stops which afford the user a tactile indication of the depth of penetration into the septum.

Referring now to FIG. 2, there is illustrated a further form of cannula 10a constructed in accordance with a preferred form of the present invention and wherein like reference numerals apply to like parts followed by the suffix "a." Cannula 10a comprises an elongated sleeve having a tip 12a, sections 14a, 16a and 18a of increasing diameter in an axial direction from the tip toward the opposite end of the cannula and tapered transition areas 20a and 22a between the respective sections. In cannula 10a, however, sections 16a and 18a have relatively reduced diameter portions or waists 40 and 42, respectively, intermediate their lengths. When the cannula 10a is inserted into the membrane and one or the other of the waists registers with the membrane, the cannula tends to remain within the membrane rather than falling out when the cannula and attached syringe are freely supported by the cannula from the membrane. With respect to these two embodiments, it will be appreciated that the waists 40, 42 can be used in conjunction with the projections and/or ribs as in FIG. 1 and/or textured surfaces. Also, when increased pressure within the system is applied as during a rapid injection, it is important to be able to maintain the cannula continuously engaged with the membrane.

Referring to FIG. 3, and in conjunction with both FIGS. 1 and 2, the proximal end of the cannula 10 or 10a is integrally connected with the adapter 24 or 24a as previously noted. Adapter 24, in turn, has male threads 50 for threaded engagement with the female threads 52 along the inside surface of the distal end of the syringe barrel 54. Proximally of the threads and on the adapter 24, 24a is an O-ring seal 56, 56a for sealing the adapter in the distal end of the syringe barrel 54. Thus, the adapter is screwthreaded into and sealed relative to the distal end of the barrel and is releasable therefrom for retraction along with the cannula into the interior of the barrel. Retraction of the adapter and cannula may be effected by any one of a number of different mechanisms. For example, the mechanisms disclosed in U.S. Pat. No. 6,033,386 of common assignee herewith and incorporated herein by reference may be used to withdraw the adapter of the cannula into the barrel.

Figure 7:
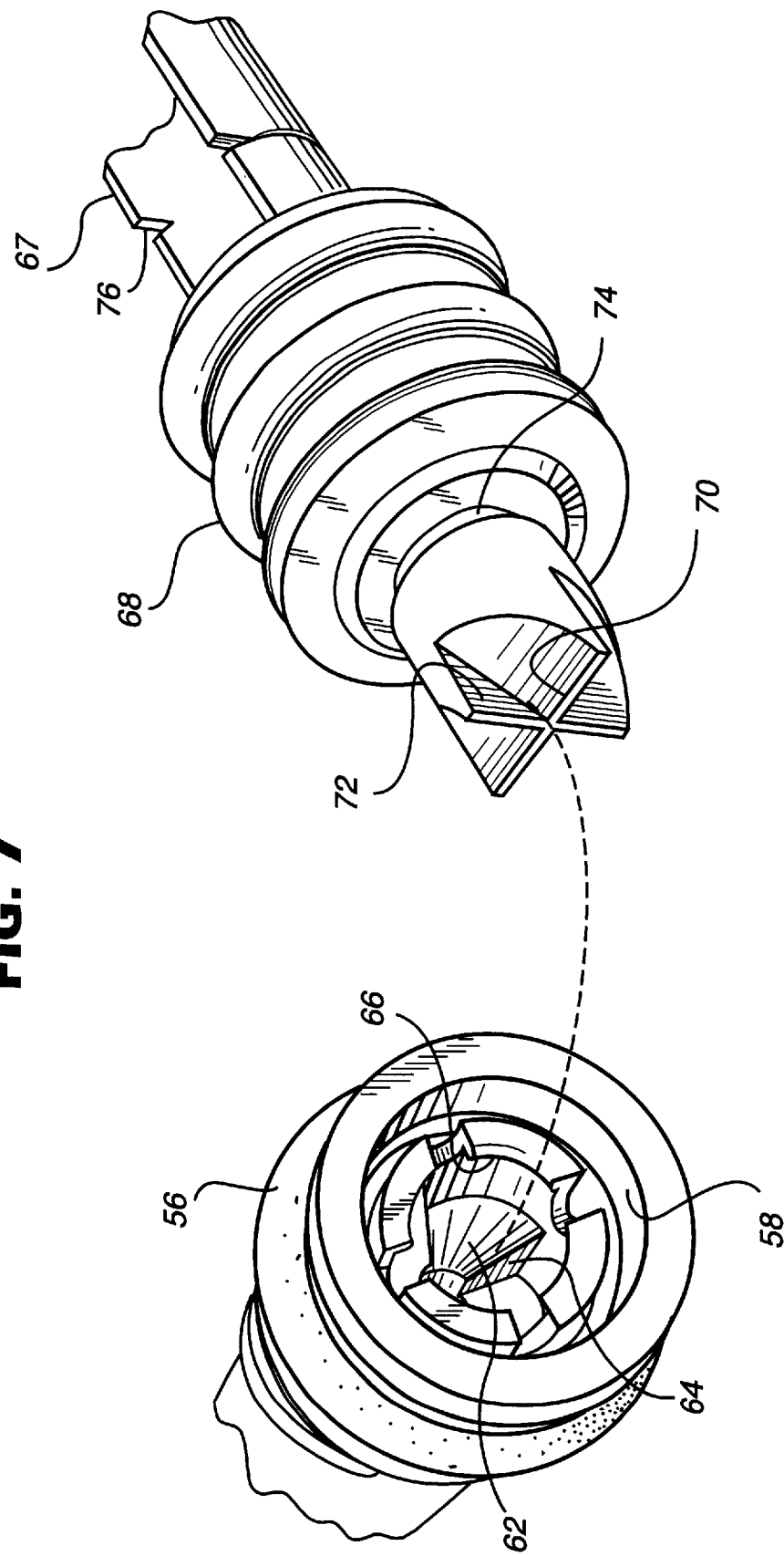
FIG. 7 is a fragmentary perspective view illustrating a preferred interconnection between a syringe plunger and adapter mounting a cannula for withdrawing the cannula into the syringe barrel after use according to the present innovation.
Figure 11:
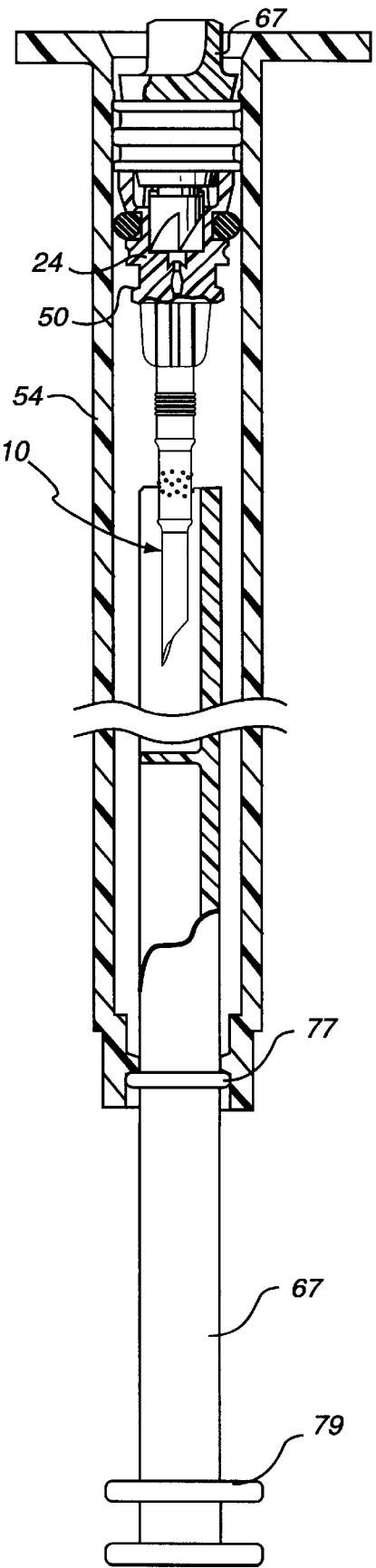
FIG. 11 illustrates a syringe with the cannula retracted and sealed within the barrel after use.

Referring to FIGS. 3 and 7, the adapter 24, 24a includes a central recess 58, the bottom of which has a central opening 60 in communication with the passage 28 of the cannula. The adapter also includes within recess 58 plunger connective structure including alignment, drive and connective surfaces 62, 64 and 66, respectively. The alignment surfaces 62 include arcuate sloping surfaces, while the drive surfaces 64 comprise radial and axially extending flat surfaces. The connective surfaces 66 include radially inwardly projecting arcuate ribs or flanges spaced axially from the alignment and drive surfaces 62 and 64, respectively, and circumferentially from one another. The distal end of the plunger 67 is illustrated in FIG. 7 and includes a bung 68 and adapter connective structure including alignment surfaces 70, drive surfaces 72 and connective surface 74, generally complementary to the alignment, drive and connective surfaces 62, 64 and 66, respectively, of the adapter. Upon displacement of the plunger toward the adapter, the alignment surfaces 70 and 62 engage one another to rotate the plunger and adapter relative to one another to bring the drive surfaces 64 and 72 into contact with one another. Simultaneously, the ribs 66 engage in the annular groove 74 of the plunger. With the engagement and joint rotation of the plunger and adapter relative to the barrel 54, the adapter is unthreaded from the barrel and can be withdrawn axially, carrying the cannula 10 with the adapter into the interior of the barrel. As in the above-referenced prior patent, the plunger can be broken off at a break-off location 76 and attached to the distal end of the barrel, sealing the barrel at that end. Particularly, a rib 77 adjacent the finger press end 79 of the plunger 67 seals with the interior surface of the distal end of the barrel (FIG. 11). The bung 68 seals the barrel at its proximal end with the adapter and cannula within the interior of the barrel. The used cannula can also be sealed within the barrel using the cap which, prior to use, was placed on the front of the barrel to protect the needle or cannula.

Figure 4:
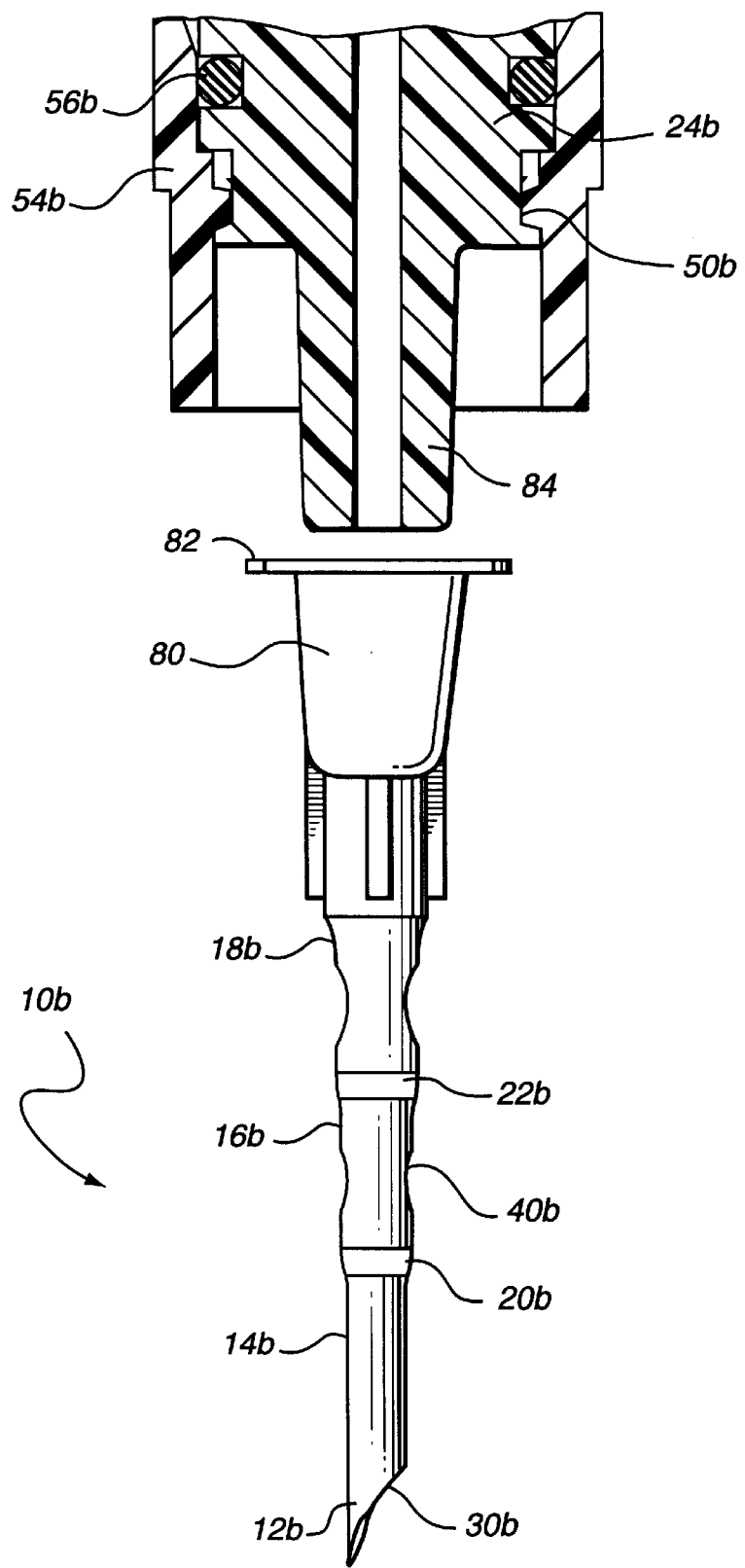
FIG. 4 is a fragmentary cross-sectional view of the end of a syringe with a cannula having a Luer fit poised for connection with the syringe.
Figure 5:
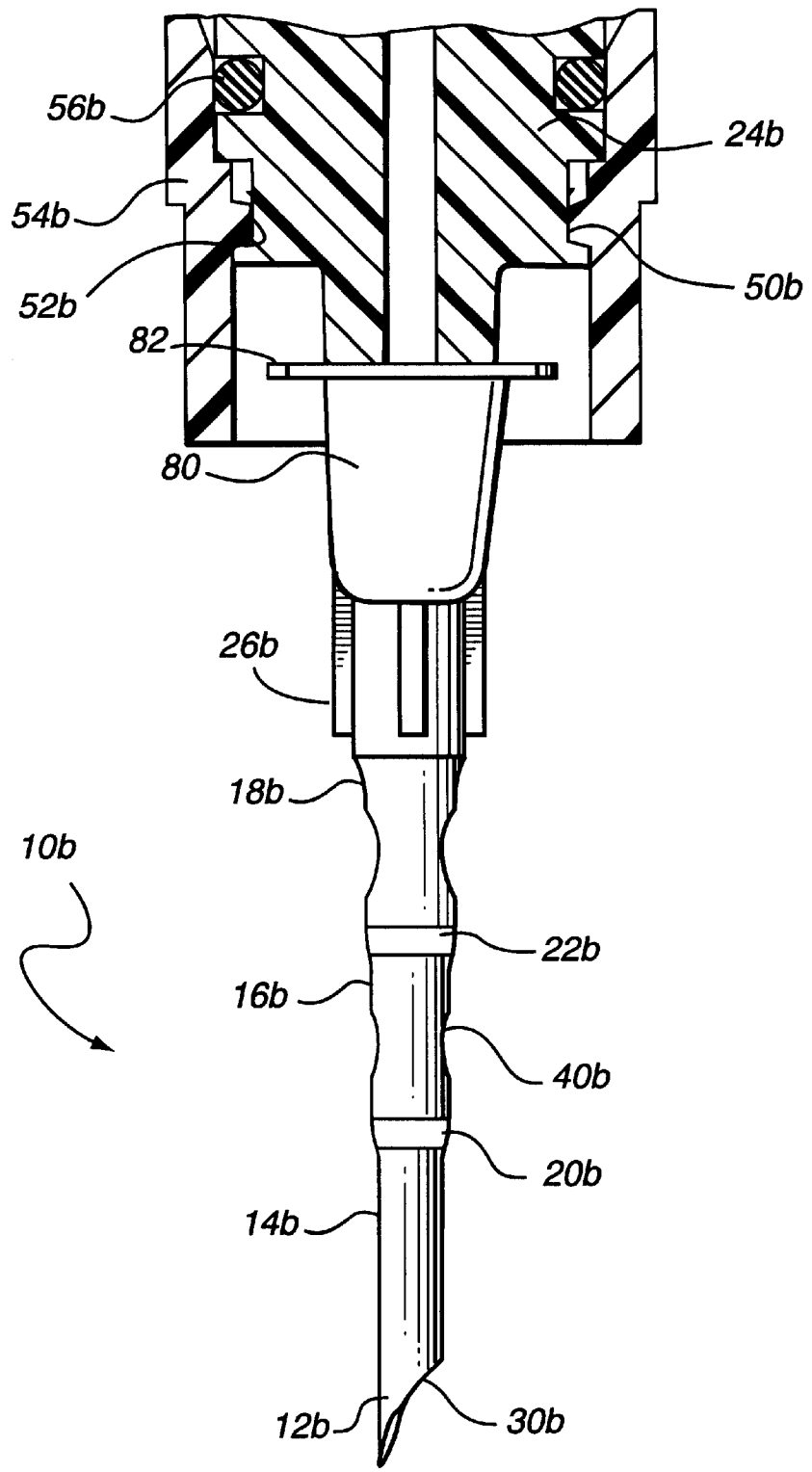
FIG. 5 is a side elevational view of the cannula fit on the adapter of the syringe of FIG. 4.

Referring now to FIG. 4, wherein like parts have like reference numerals as in the preceding embodiments, followed by the suffix "b," there is illustrated a cannula 10b of the type illustrated in FIG. 2, except that the proximal end of the cannula carries a Luer fit or lock 80. The Luer fit or lock comprises a generally conical section having a conical recess opening through its larger diameter end at the proximal end of the cannula 10b. The Luer fit or lock 80 also includes radially extending, diametrically opposite flanges 82. For those syringes having a male Luer fit at their distal ends (i.e., without female threads), the cannula 10b can be readily applied to the syringe by pressing the female Luer conical section onto a complementary tapered male part 84 of the syringe. The frictional engagement between these parts maintains the cannula on the end of the adapter. It will be appreciated that the adapter 24b is similar to adapter 24 in all respects except that adapter 24b has the tapered male part 84 at its distal end in lieu of being integral with the cannula. FIG. 5 illustrates the cannula 10b of FIG. 4 fully secured to the adapter 24b.

Figure 6:
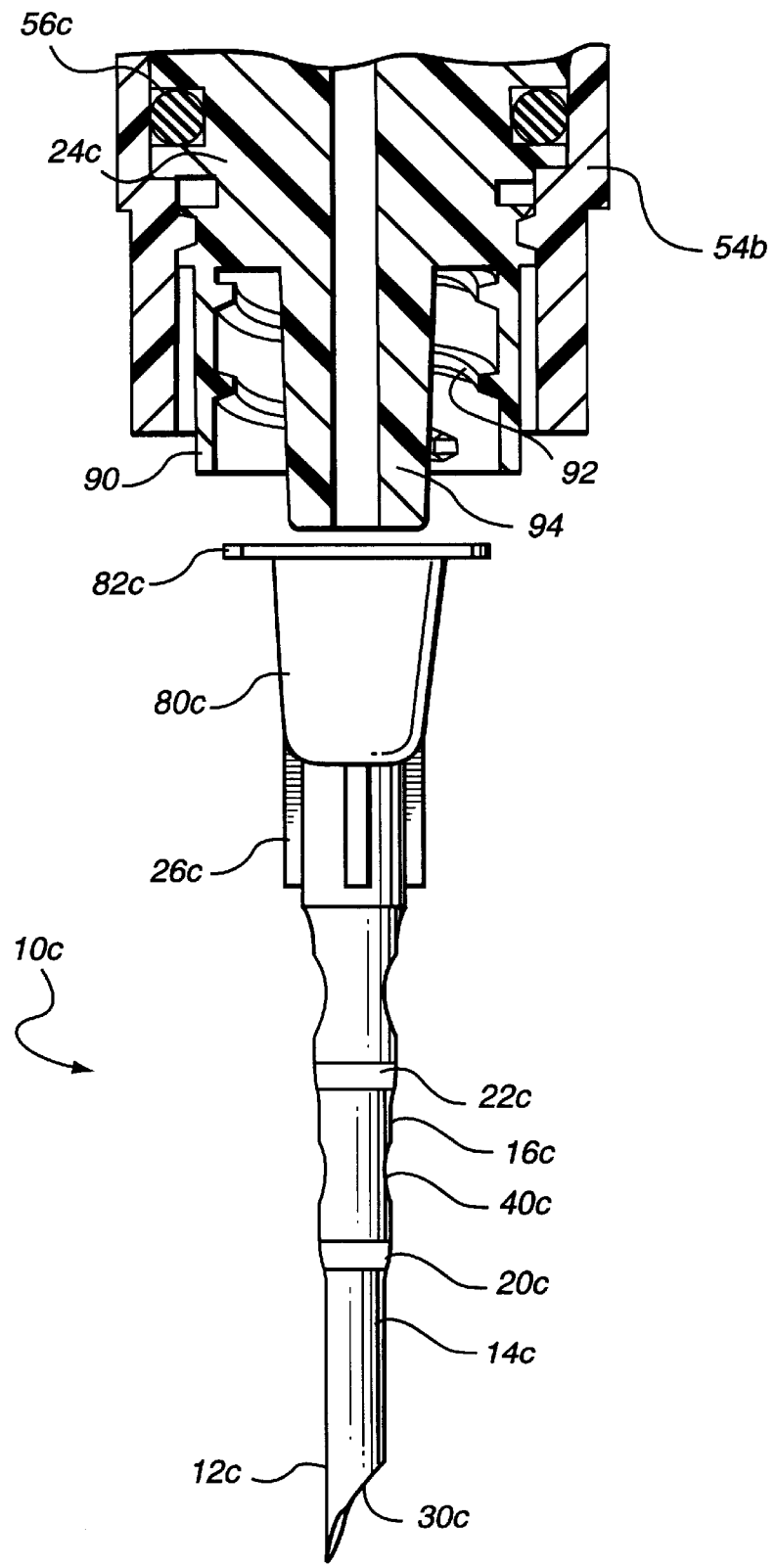
FIG. 6 is a view similar to FIG. 4 illustrating the cannula poised for securement as a Luer lock with an adapter of a syringe.

Referring to FIG. 6, there is illustrated a cannula of the type illustrated in FIG. 2 wherein like parts have like reference numerals, followed by the suffix "c." In this form, the cannula 10c is identical to the cannula 10b and has a Luer lock 80c with the end of the syringe. Particularly, the adapter 24c in FIG. 6 includes an axially extending sleeve 90 which has internal female threads 92 surrounding the male Luer conical projection 94. The Luer lock 80c is rotated onto the male projection 94 such that flanges 82c are threaded along the internal threads 92, thus securing the cannula 10c to the adapter 24c.

Referring now to FIGS. 8A–8C, the cannula 10 illustrated in FIG. 1 and integrally attached to the adapter of a syringe barrel, is illustrated being inserted into a non-pre-slit membrane or septum 100 of a medical vial 102. The septum 100 may also be pre-slit. The piercing section 14 of cannula 10 is first inserted into the non-pre-slit septum 100. Because of the reduced friction afforded by coating 32, entry of the cannula into the septum, particularly a non-pre-slit septum, is facilitated. Upon further axial pressure, the second section 16 as illustrated in FIG. 8B is received within the vial 102. Increased resistance to withdrawal of the cannula from the septum 100 resulting from the engagement of the projections 34 with the penetrated septum walls is thus afforded. Upon further axial pressure, the third section 18 may be received within the vial 102 to afford further increased resistance to withdrawal of the cannula from the vial while assuring the sealing engagement therebetween. The vial and syringe may be inverted and medication withdrawn into the syringe in the usual manner with the assurance that the cannula and vial are in sealing engagement with one another and will not separate from one another. The transition portions 20 and 22 indicate to the user in a tactile manner that the cannula is transitioning from the first section 14 to the second section 16 and subsequently from section 16 to section 18.

Figure 9A:
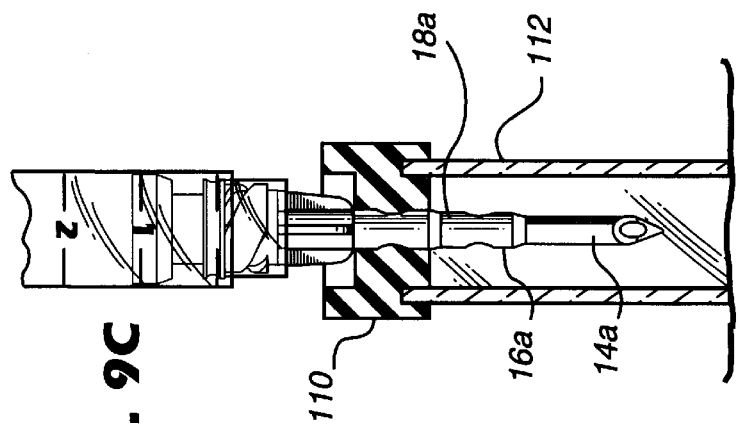
FIGS. 9A, 9B and 9C illustrate the cannula of FIG. 2 engaging through a non-pre-slit septum.
Figure 9B:
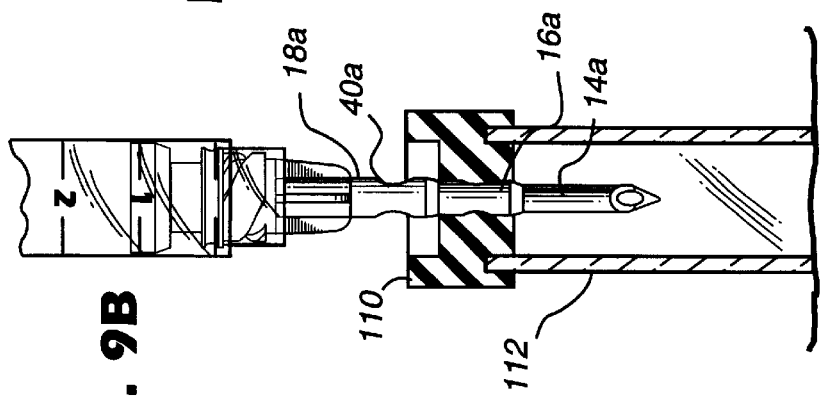
Figure 9C:
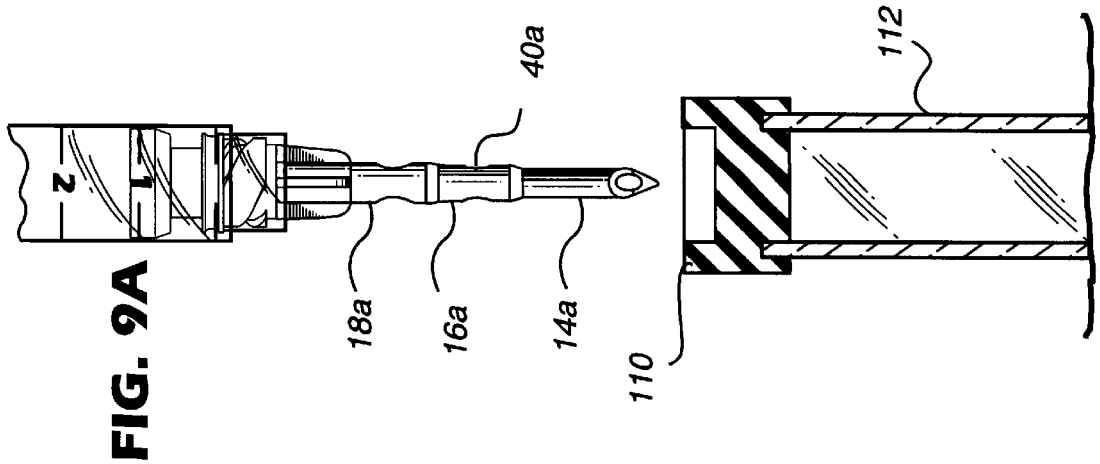

Referring to FIGS. 9A–9C, the cannula 10a is illustrated penetrating a non-pre-slit membrane, for example, the stopper 110 on an evacuated container 112. With the piercing section 14 first piercing and entering the membrane 110, the user can apply further pressure and engage in sequence the sections 16 and 18 of the cannula with the evacuated container. Consequently, it will be seen that the cannula can be used with both non-pre-slit and pre-slit septums. Also, the resistance to withdrawal of the cannula from the septum is a function of the depth of penetration of the cannula into the septum.

Figure 10:
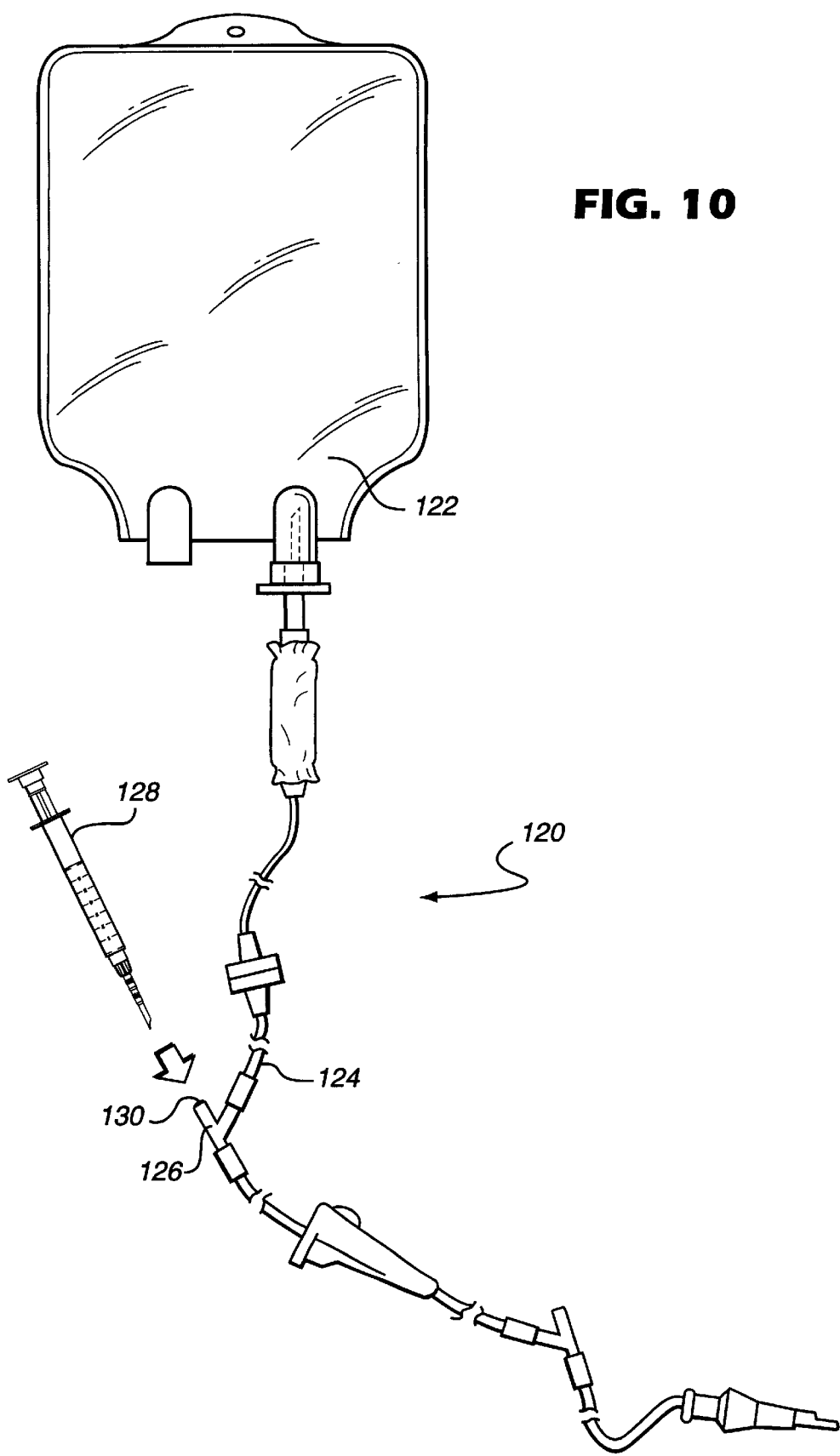
FIG. 10 illustrates an IV set illustrating a syringe for penetration of a septum in the port of an IV line.

Referring now to FIG. 10, there is illustrated an IV set 120 containing a flexible IV bag 122 and a line 124, the distal end of which is typically connected with a patient. Various ports 126 are provided along the length of the IV line 124 for fluid injection, for example, by a syringe 128. The ports 126 typically have a pre-slit septum 130 at the Y-slit in the IV line 124 and which port 126 and septum 130 may be of various sizes. It is useful as explained previously for the IV set, including the septums in the ports, to frequently support the syringe 128 from a port, for example, in the case of titrating of a fluid and giving serial aliquots of medication. The cannula 10 hereof may be used with the different physical dimensions and characteristics such as diameter and/or hardness and/or thickness of the septums currently in available IV and other ports. The different resistance to movement depending upon the depth of insertion of the cannula through the septum enables the present cannula to be used with such septums with the assurance that the cannula will not withdraw from the septum absent the user positively withdrawing the cannula. Thus, where a thin pre-slit septum is employed in a port, the cannula is inserted such that the intermediate section 16 frictionally contacts the septum. Thus, the projections 34 engaging the septum serve as an initial stop preventing the start of sliding withdrawing movement. This affords sufficient static frictional contact to support the syringe from the septum of the port. For larger thicker septums, the cannula can be inserted such that the third section engages the pre-slit walls of the septum. The static frictional contact, e.g., of the cannula ribs 36 with the walls of the septum, affords increased resistance to movement sufficient to support the syringe from the septum. Also, the cannula can be attached to the syringe and employed to penetrate the pre-slit or non-pre-slit septums of medication vials to withdraw the medication therefrom and supply the medication directly to the pre-slit septum in a portion of an IV line without any intervening additional devices.

With reference to FIG. 12, there is illustrated a cannula 10c having a body comprising an elongated sleeve having various sections 134, 136 and 138 separated axially from one another by larger diameter transition sections 140 and 141. The sections 134, 136 and 138 may be similar to sections 14, 16 and 18 of the preceding embodiments, i.e., sections of increasing diameter in a direction away from the tip of the cannula, or may have identical diameters as illustrated in FIG. 12. The transition sections 140 and 141 may have different diameters relative to one another, the diameter of section 141 preferably being greater than the diameter of section 140.

From a review of drawing FIG. 12, it will be appreciated that the slopes of the transition sections 140 and 141 along their forward surfaces 144 and 146, respectively, facing tip 12c are different. The surface 144 slopes outwardly from the sleeve to a lesser extent than the sloped surface 146. The surfaces 144 and 146 thus offer different resistance to movement of the cannula body through the septum or membrane. Also, the back or rear surfaces 148 and 150 of transition section 140 and 141, respectively, are different from one another. The sloped surface 148 offers less resistance to withdrawal of the cannula body from the septum or membrane than the surface 150, which lies substantially at right angles to the axis of the cannula body.

The resistance to axial movement of the cannula body through a septum or membrane in one direction may therefore be different from the resistance to movement of the cannula body through the septum or membrane in the opposite direction. Also, there are differences in resistance to movement in any one direction. Thus, the illustrated transition sections 140 and 141 afford differential, e.g., increasing resistance to movement in a direction of axial inserting movement of the cannula body through the membrane or septum into a vial, whereas movement of the cannula body relative to the membrane or septum in an opposite direction, e.g., withdrawing the cannula body from the vial capped by the membrane or septum, may provide a greater resistance to withdrawal than either transition section 140 or 141 affords upon insertion. This is particularly useful when the cannula with attached syringe is left for support solely from the membrane or septum. The surfaces 148 and 150 also provide differential resistance to movement in the opposite, i.e., withdrawing, direction relative to the septum or membrane. Alternatively, the shape of the surfaces 148 and 150 along the back sides of the transition sections 140 and 141, respectively, can be altered to increase or decrease the resistance to movement of the cannula body through the membrane or septum. For example, a more gentle slope along the surfaces 148 and 150 of the transition sections 140 and 141, respectively, affords less resistance than the illustrated relatively sharp slopes along the illustrated surfaces 148 and 150. It will thus be appreciated that the transition sections 140 and 141 may have different resistances to movement of the cannula body relative to the membrane or septum in either direction and differential resistance to movement in any one direction depending upon the depth of penetration of the cannula body in the septum or membrane. By changing the configuration of the forward and rear surfaces 148 and 150 of the transition sections 140 and 141 engaging the membrane or septum, the degree of resistance to movement, e.g., either withdrawal or insertion, can be changed. As noted previously, the transition sections 140 and 141 may be utilized with any of the preceding embodiments of the invention. Particularly, the sleeve sections 134, 136 and 138 may comprise any of the sleeve sections 14, 16, 18; 14a; 16a, 18a; 14b, 16b and 18b; and 14c, 16c and 18c of the previous embodiments.

It will be appreciated that the transition sections in each of the embodiments hereof need not comprise annular surfaces and may comprise segmented, circumferentially extending surfaces, e.g., as illustrated by the transition section segments 150 of FIG. 13. Segmented surfaces facilitate insertion and withdrawal of the cannula body relative to the membrane M. For example, the cannula body can be canted or angled relative to the surface of the septum or membrane with the space between the segments first engaging the membrane, offering less resistance to movement of the cannula body relative to the membrane or septum.

Further, transition sections or ribs may be provided on the cannula body at locations to capture and releasably lock the membrane or septum surface between the axially spaced transition sections. For example, the opposing surfaces 152 and 154 (FIG. 13) of the transition sections may comprise flat, annular surfaces slightly exceeding the thickness of the membrane M. As the cannula body is moved to insert or withdraw the cannula body relative to the membrane, the margins of the membrane or septum about the opening may be captured between the right angularly related surfaces 152 and 154 of the transition sections. This affords substantial resistance to movement of the cannula body in either direction relative to the membrane or septum.

To facilitate movement of the cannula body through a membrane or septum, particularly a pre-slit membrane or septum, the transition sections can be formed in a shape having a lateral dimension in one direction greater than a right angularly related lateral dimension. For example, on a cylindrical cannula body, the transition section can be in the form of an oval or even rectilinear, with orthogonally related long and short axes, as viewed axially. Hence, the long axis of the oval or rectilinear transition section can be aligned in the direction of a slit in the membrane or septum, i.e., in registration with the slit, facilitating movement of the cannula body relative to the membrane or septum. Conversely, alignment of the smaller dimension of the oval or rectilinear-shaped transition section in the direction of and in registration with the slit of the membrane or septum affords increased resistance to movement of the cannula body relative to the membrane or septum. The alignment can be accomplished by rotating the cannula body relative to the membrane or septum to align or misalign alignment marks on the cannula body and the membrane or septum.

Further, the cannula body sleeve may have a cross-sectional configuration perpendicular to its axis different than cylindrical. For example, the cannula body sleeve may have an oval or rectilinear, e.g., square, cross-sectional configuration, to afford additional surface area which further increases resistance to movement relative to a membrane or septum and also further inhibits or minimizes any tendency of the blunt cannula to penetrate an individual's skin or the rubber gloves used in surgical procedures.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A cannula for use with a syringe and for insertion through a membrane, comprising:

a cannula body including an elongated sleeve and having a central axial passage therethrough for transmitting a fluid between opposite ends thereof;

said sleeve terminating in a tip at one end with said passage opening axially through said tip;

an opposite end of said sleeve adapted for connection with the syringe;

mechanical formations formed on an outer surface of said cannula body along one of first and second axially spaced sections along said sleeve affording respective differential resistances to movement relative to the membrane as a function of the death of penetration of the cannula body relative to the membrane, said first section being located axially intermediate said tip and said second section;

a transition section between said first and second sections having a diameter larger than the diameters of said first and second section; and a third section of said sleeve having an increased diameter relative to said second section and a transition section between said second section and said third section having a diameter larger than the diameter of said first section and said second section.

2. A cannula according to claim 1 wherein said mechanical formations provide an increase in resistance to movement relative to the membrane as a function of increasing distance from said one end of said cannula body.

3. A cannula according to claim 1 wherein one of said mechanical formations includes a plurality of projections axially spaced from one another along an outer surface of said sleeve along said second section.

4. A cannula according to claim 3 wherein said projections comprise a plurality of ribs spaced axially from one another.

5. A cannula according to claim 1 wherein one of said first and second sections has a reduced diameter portion relative to the diameter of said one of said first and second sections.

6. A cannula according to claim 1 wherein said mechanical formations comprise different surface textures at axially spaced locations along said sleeve.

7. A cannula according to claim 1 wherein said opposite end of said sleeve includes a Luer connector.

8. A cannula according to claim 1 wherein said opposite end of said sleeve includes a generally cup-shaped connector integrally formed with said sleeve and having a pair of radially outwardly directed diametrically opposite flanges.

9. A cannula according to claim 1 wherein said opposite end of said sleeve forms an integral part of an adapter for sealing an end of a syringe barrel, said adapter including an externally threaded portion for releasable threaded engagement with threads on the end of the syringe barrel.

10. A cannula according to claim 1 in combination with said syringe, said syringe including a barrel, an adapter releasably secured to the barrel at a distal end thereof for carrying said cannula body, a plunger extending through the opposite end of the barrel for axial movement relative to the barrel, said adapter and plunger having respective connective structures for coupling the plunger and adapter to one another in response to displacement of the plunger relative to the barrel into engagement with the adapter and for withdrawing the adapter and cannula body into the barrel in response to displacement of the plunger and adapter in a direction away from the distal end of the barrel.

11. The combination of claim 10 wherein said opposite end of said sleeve includes a Luer connector for securing the cannula body and adapter to one another.

12. The combination of claim 10 wherein said opposite end of said sleeve includes a generally cup-shaped connector integrally formed with said sleeve and having a pair of radially outwardly directed diametrically opposite flanges, said adapter having female threads for threadedly receiving the flanges of said connector for securing the cannula body and adapter to one another.

13. The combination of claim 10 wherein said opposite end of said sleeve forms an integral part of an adapter for sealing an end of a syringe barrel, said adapter including an externally threaded portion for releasable threaded engagement with threads on the end of the syringe barrel.

14. A cannula according to claim 1 wherein one of said second and third sections has a reduced diameter portion relative to the diameter of said one of said second and third sections.

15. A cannula according to claim 1 wherein said tip is sufficiently sharp to pierce a non-slit membrane and sufficiently blunt to avoid penetration of an individual's skin.

16. A cannula for use with a syringe and for displacement through a membrane, comprising:

a cannula body including an elongated sleeve formed of a plastic material and having a central axial passage therethrough for transmitting a fluid between opposite ends thereof;

said sleeve terminating in a tip at one end with said passage opening axially through said tip;

an opposite end of said sleeve adapted for connection with the syringe;

first and second axially spaced sections along said sleeve, said first section being located axially intermediate said tip and said second section;

a transition section between said first and second sections having a diameter larger than the diameters of said first and second sections;

said transition section having a first surface facing said tip and a second surface on a side thereof opposite said first surface, said first and second surfaces affording respective differential resistance to movement in opposite directions relative to the membrane;

said first surface being configured to provide a first magnitude of resistance to movement of said cannula body through the membrane in a first axial direction, said second surface being configured to provide a second magnitude of resistance to movement of said cannula body through the membrane in a second axial direction opposite said first axial direction and different than the first magnitude of resistance to movement.

17. A cannula according to claim 16 wherein said first and second surfaces join one another along a maximum diameter of said transition section and have different radii extending from the maximum diameter to the first and second surfaces, respectively.

18. A cannula according to claim 16 wherein said second section has a diameter greater than the diameter of said first section.

19. A cannula according to claim 16 wherein said first and second sections have surfaces affording differential resistance to movement relative to the membrane as a function of the depth of penetration of the sleeve through the membrane.

20. A cannula for use with a syringe and for displacement through a membrane, comprising:

a cannula body including an elongated sleeve formed of a plastic material and having a central axial passage therethrough for transmitting a fluid between opposite ends thereof;

said sleeve terminating in a tip at one end with said passage opening axially through said tip;

an opposite end of said sleeve adapted for connection with the syringe;

first and second axially spaced sections along said sleeve, said first section being located axially intermediate said tip and said second section;

a transition section between said first and second sections having a diameter larger than the diameters of said first and second sections;

said transition section having a first surface facing said tip and a second surface on a side thereof opposite said first surface, said first and second surfaces affording respective differential resistance to movement in opposite directions relative to the membrane; and a third section of said sleeve and a second transition section between said second section and said third section having a diameter larger than the diameters of said first, second and third sections.

21. A cannula according to claim 20 wherein said second transition section has a first surface on a side thereof opposite said first surface thereof, said first and second surfaces of said second transition section affording respective differential resistance to movement in opposite directions relative to said membrane.

* * * * *